United States Patent [19]

Carney

[11] Patent Number: 5,780,510
[45] Date of Patent: Jul. 14, 1998

[54] 2,4-DISULFO PHENYL BUTYL NITRONE, ITS SALTS AND THEIR USE AS PHARMACEUTICALS

[75] Inventor: John M. Carney, Lexington, Ky.

[73] Assignees: Oklahoma Medical Research Foundation, Oklahoma City, Okla.; University of Kentucky Research Foundation, Lexington, Ky.

[21] Appl. No.: 663,316

[22] PCT Filed: Dec. 22, 1994

[86] PCT No.: PCT/US94/14545

§ 371 Date: Jun. 19, 1997

§ 102(e) Date: Jun. 19, 1997

[87] PCT Pub. No.: WO95/17876

PCT Pub. Date: Jul. 6, 1995

Related U.S. Application Data

[63] Continuation-in-part of Ser. No. 173,579, Dec. 23, 1993, Pat. No. 5,488,145.

[51] Int. Cl.[6] .................................................. A61K 31/185
[52] U.S. Cl. ...................... 514/576; 514/658; 562/62; 564/282
[58] Field of Search ............................ 514/576, 658; 564/282; 562/66

[56] References Cited

U.S. PATENT DOCUMENTS

| 5,475,032 | 12/1995 | Carney | 514/576 |
| 5,488,145 | 1/1996 | Carney | 562/62 |
| 5,508,305 | 4/1996 | Carney | 514/517 |

*Primary Examiner*—James H. Reamer
*Assistant Examiner*—Dwayne C. Jones

[57] ABSTRACT

2,4-disulfonyl α-phenyl-tert-butyl nitrone and its pharmaceutically acceptable salts are disclosed. These materials are useful as pharmaceutical agents for oral or parenteral, e.g. intravenous administration to patients suffering from acute central nervous system oxidation as occurs in a stroke or from gradual central nervous system oxidation which can exhibit itself as progressive central nervous system function loss. The materials are also used to ameliorate the side effects of oxidative-damage causing antineoplastic disease treatments.

40 Claims, 6 Drawing Sheets

2,4-DISULFO PHENYL BUTYL NITRONE, ITS SALTS AND THEIR USE AS PHARMACEUTICALS

CONTINUING DATA

This application is a continuation-in-part (CIP) of Ser. No. 08/173.579, filed on Dec. 23, 1993, now U.S. Pat. No. 5,488,145.

BACKGROUND OF THE INVENTION

This invention relates to a particular nitrone compound and its salts and their advantageous use as pharmaceutical nitrone free radical trapping agents.

Alpha-phenyl tert butyl nitrone

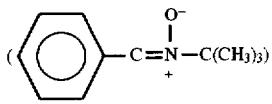

or "PBN") was identified in the 1970s as a useful analytical reagent to be used in conjunction with electron spin resonance ("ESR") to aid in the detection of free radicals. PBN was found to react with certain free radicals and generate a chemical species yielding a characteristic ESR spectrum and thus making it possible to determine the presence or absence of free radicals.

In the late 1970s and early 1980s the medical community began to focus on the roles played by free radicals in diseases such as heart attacks, strokes and the like. PBN was used increasingly in vitro to provide analytical evidence of the presence of free radicals in these settings. It was also later administered in vivo in animal models, again as an analytical adjunct in attempts to observe free radicals during ischemia simulations and the like.

In the mid 1980s, the first possible therapeutic effects of PBN were implied when severe trauma ischemia animal tests showed that PBN-treated animals were more likely to survive than controls.

On May 2, 1991, PCT patent application WO-91-05552 was published. This patent application, which in part corresponds to now-issued U.S. Pat. Nos. 5,825,032 and 5,036,097, described PBN and a family of PBN derivatives defined by the formula

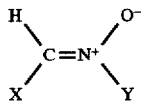

wherein

X is phenyl or

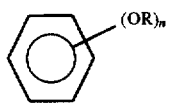

where R is H,

or Z; or

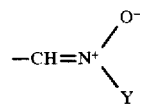

and n is a whole integer from 1 to 5 or

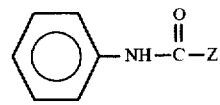

and Y is tert-butyl or a hydroxylated or acetylated tert-butyl or a substituted phenyl. These compounds were proposed as pharmaceutical agents to treat the aftermath of stroke and other conditions reported to be associated with free radical damage.

In 1992 a second PCT patent application was filed directed to PBN and related compounds and their medical use. This application, based on prior U.S. patent application Ser. No. 716,952 (filed Jun. 18, 1991), was published on Dec. 23, 1992 as WO 92/22290. This 1992 publication provided two extremely broad and general disclosures. First, it attempted to describe as many disease states as possible which were associated with free radicals. These ranged from CNS conditions (including stroke, aging, migraine, etc.) through peripheral organ disease (including atherosclerosis, bed sores, wounds, and muscle overexertion) through UV exposure, to mention but a few highlights. Second, it attempted to list as many potential spin traps as possible.

In addition to a whole range of non-PBN materials, this application greatly expanded the definition of potentially useful PBN compounds to include PBN, and derivatives thereof of the formula

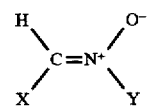

wherein

X is phenyl, imidazolyl, phenothiazinyl or

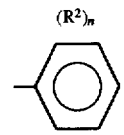

n=1–5, preferably 1–3;

$R^2$=independently (can vary within the molecule) halogen, alkyl, oxyalkyl, alkenyl, oxyalkenyl, OH, $NH_2$, NHZ, $NZ_2$, NO,

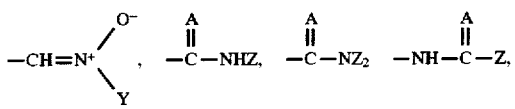

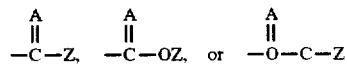

—$SO_3H$, —$OSO_3H$, SH, —S(alkyl), —S(alkenyl, and haloalkyl, specifically including —$CF_3$;

A=O or S; and

Z is a $C_1$ to $C_6$ straight, branched, alkyl or cyclic group; and

Y is a tert-butyl group that can be hydroxylated or acetylated at one or more positions; phenyl or

PBN was stated to be the most preferred compound at that time, being said to have no measurable effect on normal or uninjured cells, and a number of derivatives were also stated to be useful, including hydroxy derivatives, especially 2-, 3- or 4-hydroxyphenyl t-butyl nitrone and phenyl (mono-, di- or trihydroxy) tert-butyl nitrone; PBN esters, especially esters which release 2-, 3-, or 4-hydroxyphenyl t-butyl nitrone such as acetoxy derivative; 2-, 3-, or 4-carboxyphenyl t-butyl nitrone; phenyl hydroxybutyl nitrone; alkoxyl derivatives, especially alkoxyl derivatives which release 2-, 3-, or 4-hydroxyphenyl t-butyl nitrone, for example, the 2-, 3-, or 4-methoxyphenyl derivatives of PBN; and acetamide derivatives, especially acetamide derivatives which release 2-, 3-, or 4-aminophenyl t-butyl nitrone; diphenyl nitrone (PPN) and the analogous diphenyl nitrone derivatives; N-tert-butyl-α-(4-nitro-phenyl) nitrone; and N-tert-butyl-α-(2-sulfophenyl) nitrone.

STATEMENT OF THE INVENTION

It has now been discovered that one particular PBN derivative and its salts have unexpectedly superior pharmacological properties. Although this derivative, 2,4-disulfo PBN, falls within the broad family of materials generally described in the aforementioned WO 92/022290 publication, it is not specifically disclosed. Neither are its advantageous properties predicted.

The present compound with its two sulfonate groups was expected to exhibit improved water solubility but was also expected to exhibit poor transport across the blood/brain barrier because of its lipophobic character. However, when the present compound was made and tested in vivo, it showed an unexpected increase in efficacy as compared to PBN. This increase in efficacy occurred along with an increase in potency as compared to PBN. In direct contrast to this marked increase in potency and efficacy there was a marked and highly significant decrease in toxicity as compared to PBN.

These results were unexpected because in the general literature on structure/activity relationships within specific defined families of compounds therapeutic potency typically covaries with toxicity. Thus, most related compounds maintain their ratio of therapeutic potency to toxicity. In contrast, the compound of this invention deviates from this expected relationship when its potency increased and its toxicity decreased relative to closely related analogs.

Accordingly, in one aspect, the invention provides the PBN-disulfonyl compound

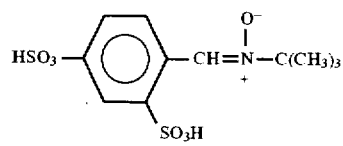

and its pharmaceutically acceptable salts.

In a second aspect, the invention provides parenterally-, e.g. intravenously- and orally-administrable pharmaceutical compositions having this compound or its salt as active ingredient.

In a third aspect, this invention provides a method for treating a patient who is suffering from a condition involving acute oxidative damage to the central nervous system, such as a patient who has suffered a stroke, in which a pharmaceutical composition based on this compound or its salt is administered parenterally, e.g. intravenously.

In a fourth aspect, this invention provides a method for treating a patient suffering from a condition characterized by protracted low grade oxidative stress upon the central nervous system and progressive loss of central nervous system function. In this method, a pharmaceutical composition based on this compound or its salt is administered parenterally, e.g. intravenously or preferably orally.

In a fifth aspect, this invention provides a method for reducing or ameliorating the side-effects arising from oxidative damage produced in a patient by cancer therapy. In this method a pharmaceutical composition based on this compound or its salt is administered parenterally, e.g. intravenously or orally.

DETAILED DESCRIPTION OF THE INVENTION

This Detailed Description is arranged into the following sections:

Brief Description of Drawings.
The Compounds and Salts.
Compound Preparation.
Pharmaceutical Compositions.
Conditions Treated and Treatment Regimens.
Examples.

BRIEF DESCRIPTION OF THE DRAWINGS

Figure 1:
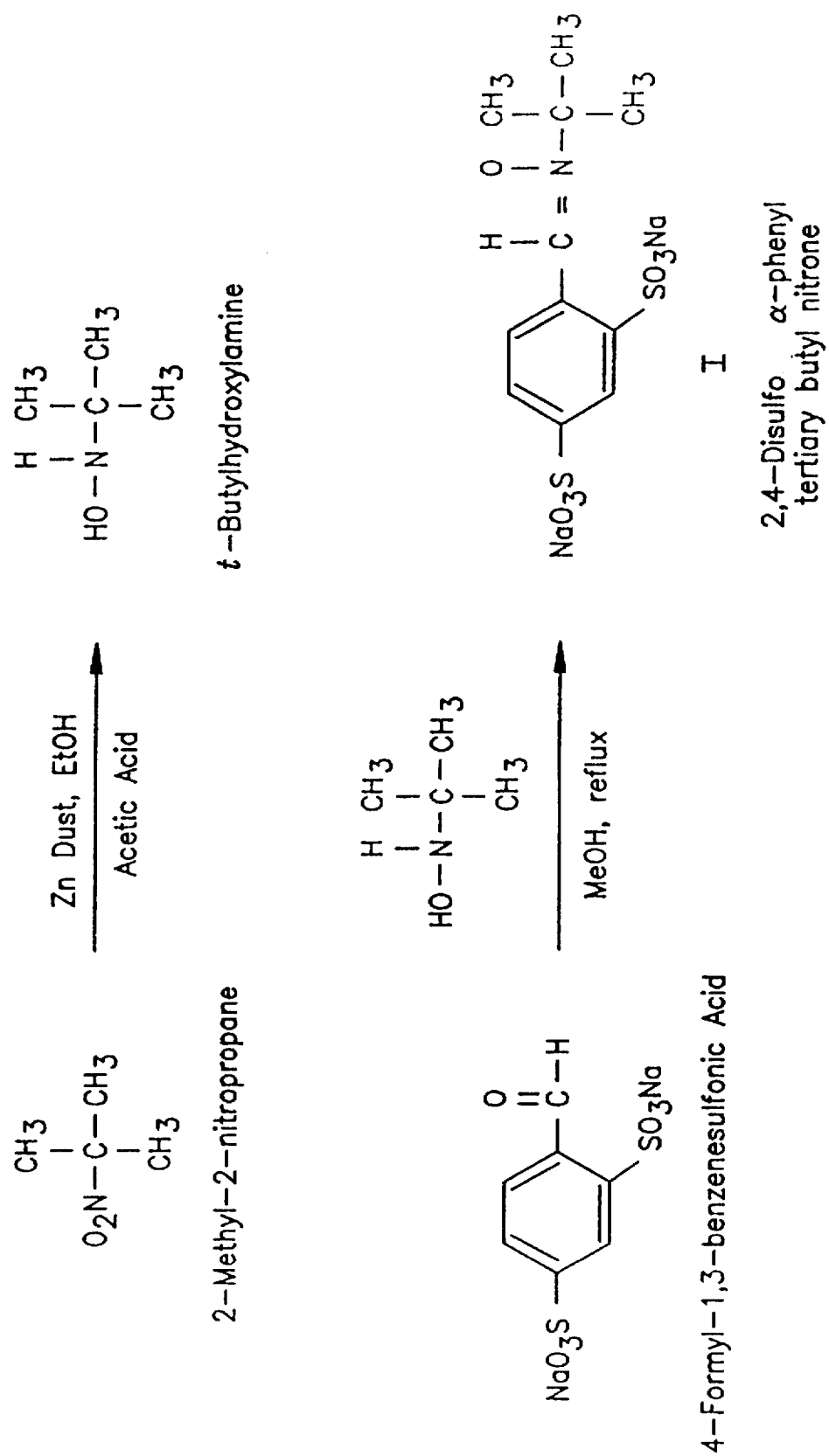

In this specification reference will be made to the accompanying drawings in which FIG. 1 is a schematic flow chart of the reactions used to prepare the compound.

Figure 2A:
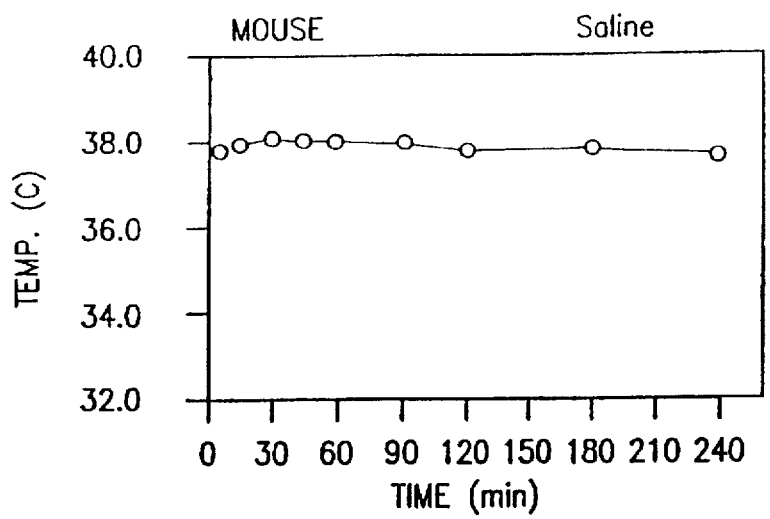
Figure 2B:
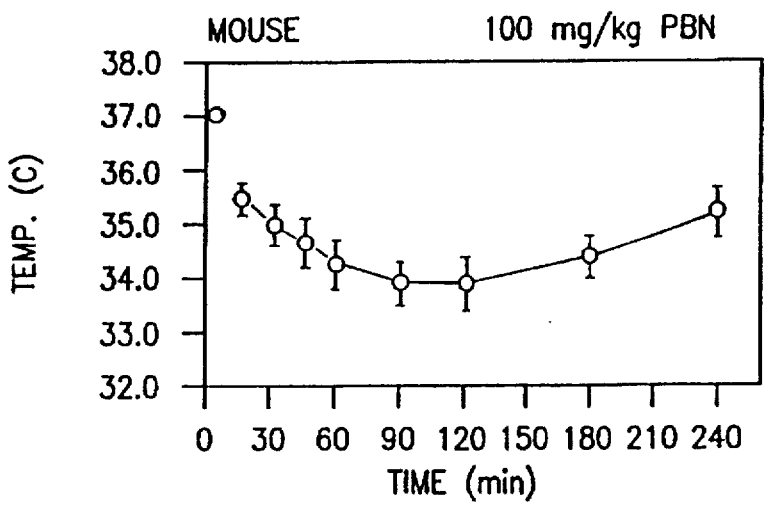
Figure 2C:
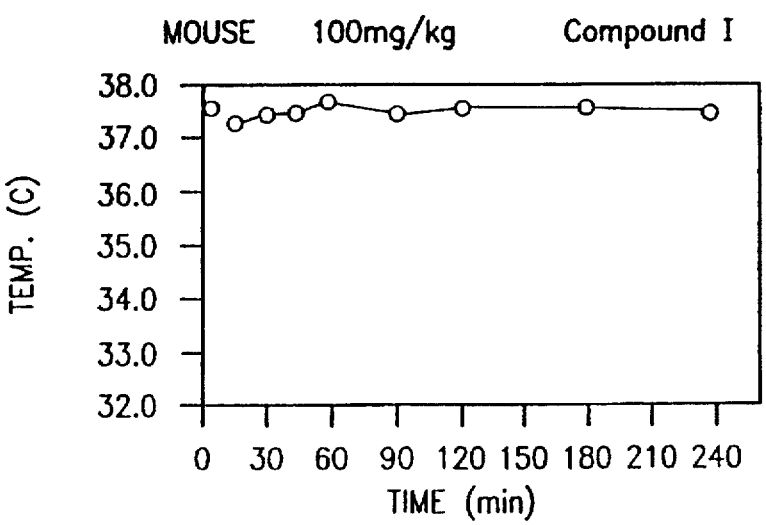
Figure 3A:
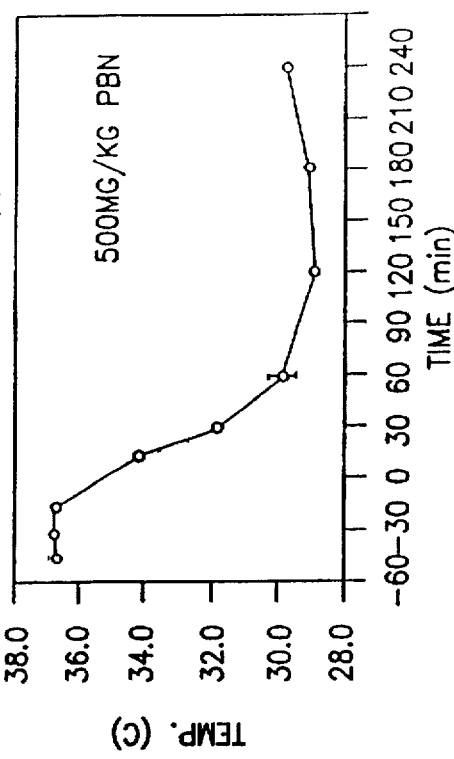
Figure 3C:
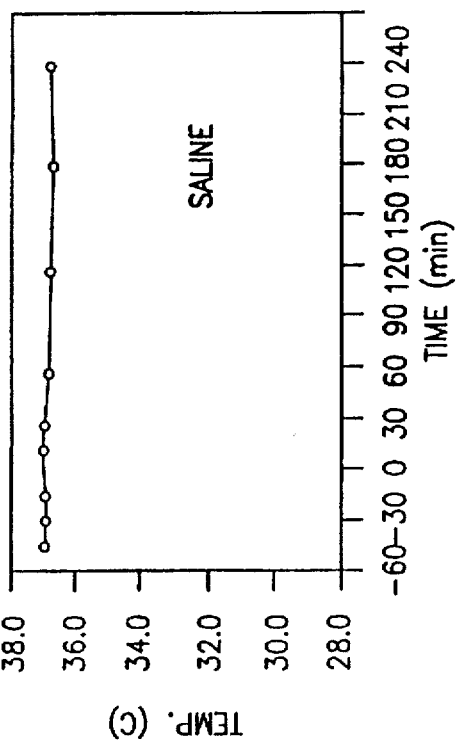
Figure 3B:
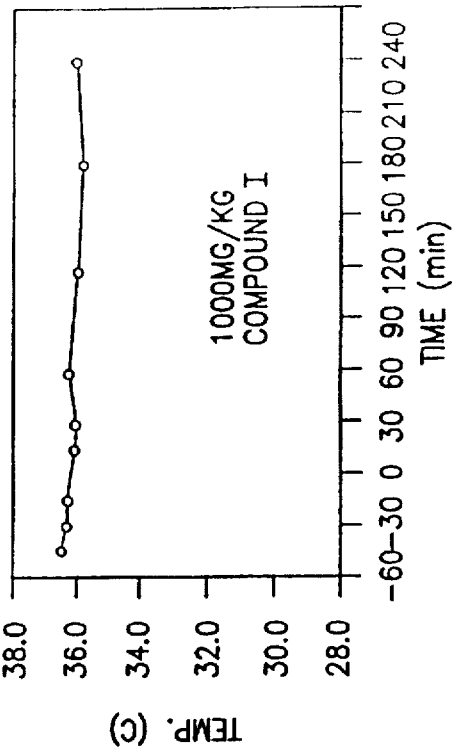
Figure 3D:
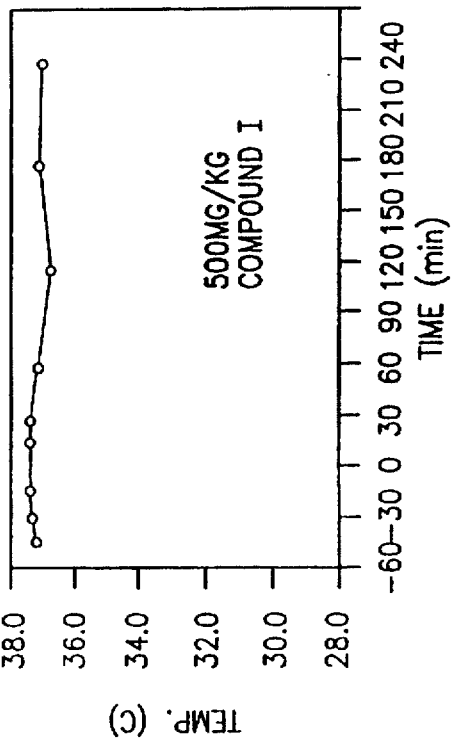
Figure 4A:
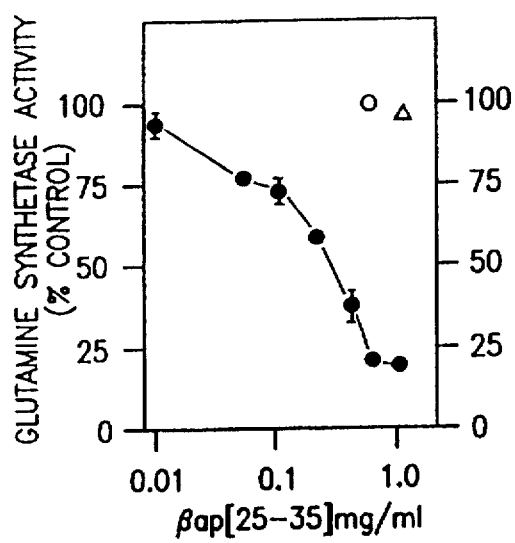
Figure 4B:
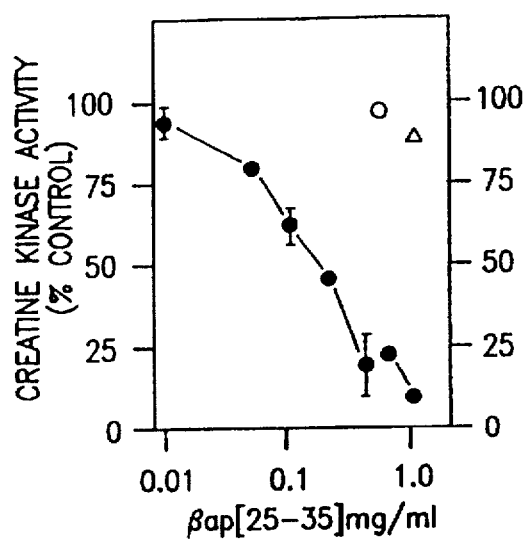
Figure 4C:
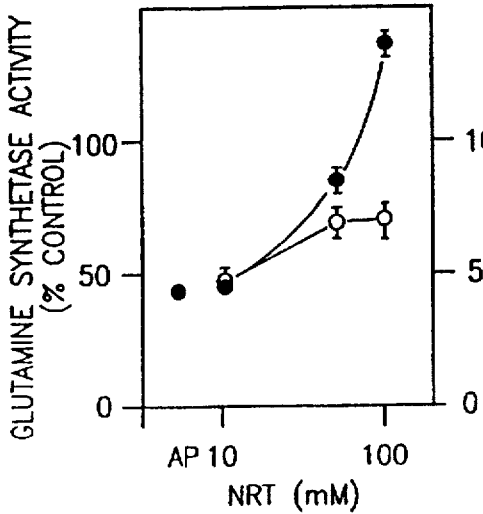
Figure 4D:
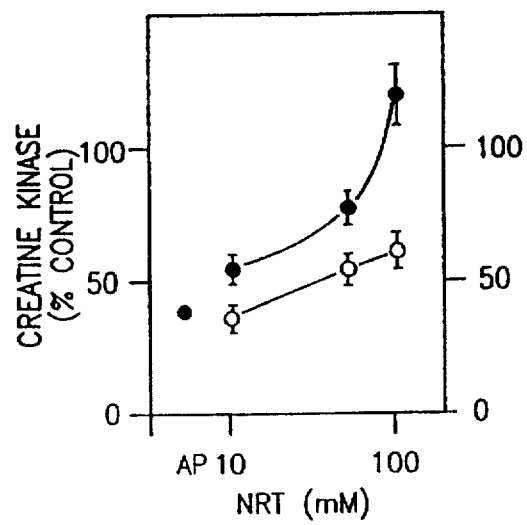

FIGS. 2 (A, B and C) and 3 (A, B, C, and D) are two sets of graphs illustrating the undesirable change in animal body thermal regulatory ability which occurs as a function of dose level with a prior art nitrone radical trapping agent and contrasting this with the lack of such undesired toxic effect with the compound of the invention.

FIG. 4 (A, B, C, and D) is a set of four graphs demonstrating the superiority of the compound of the invention as compared to a closely related prior art nitrone compound in the treatment of gradual neurodegeneration conditions (such as Alzheimer's disease) as illustrated by their relative ability to interfere with beta amyloid protein's inactivation of key enzymes in solution.

Figure 5:
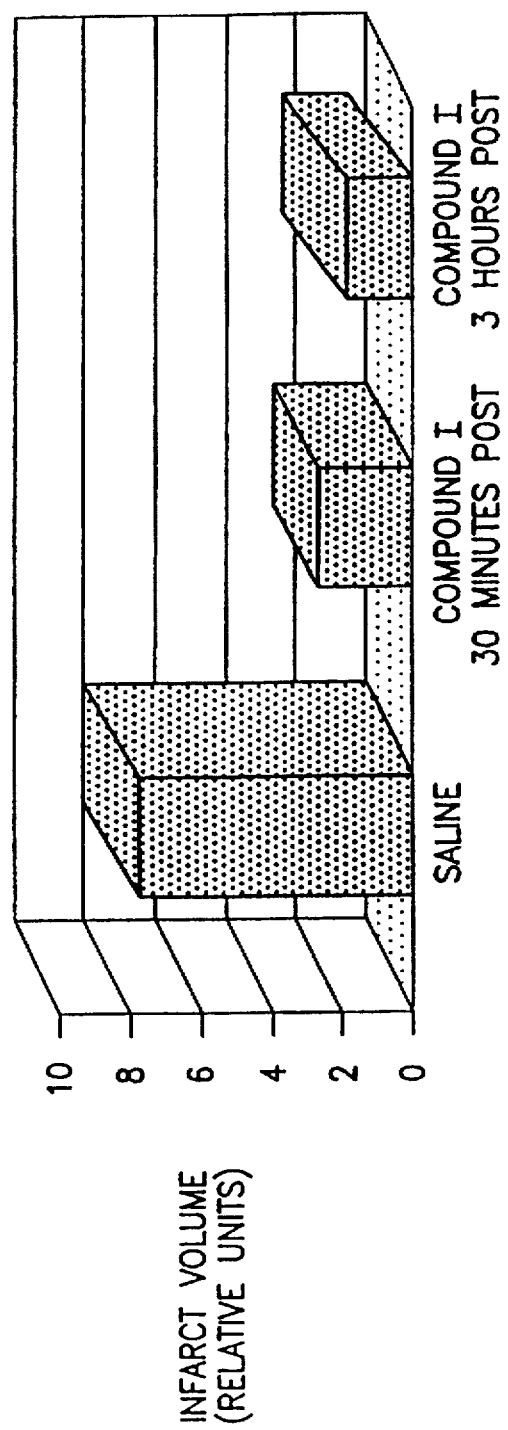

FIG. 5 is a graph illustrating the effectiveness of the compound of the invention in reducing the ultimate infarct volume observed following middle cerebral artery occlusion in rats.

Figure 6A:
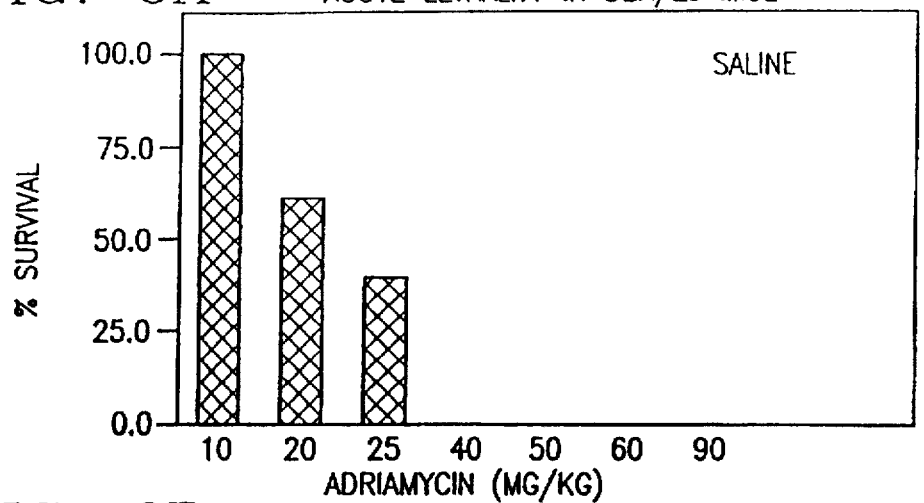
Figure 6B:
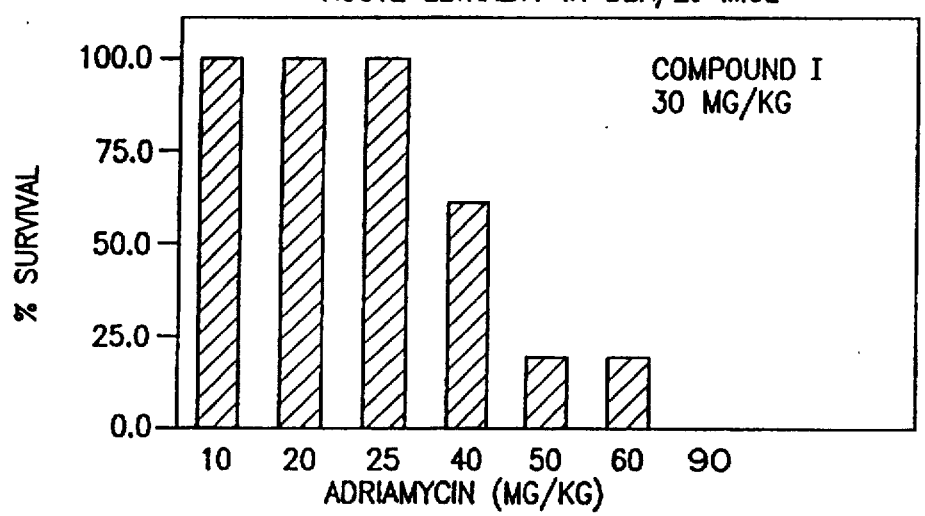
Figure 6C:
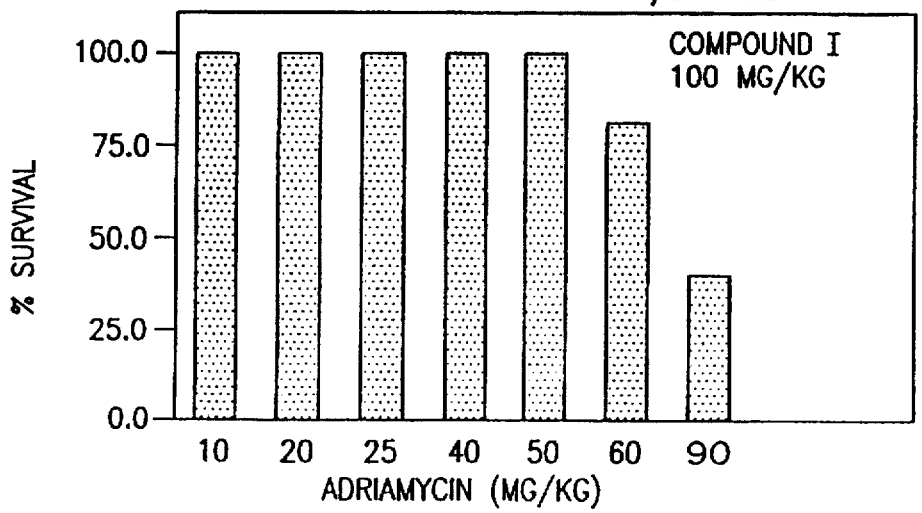

FIGS. 6 (A, B and C) are three graphs illustrating the ability of the compound of the invention to reduce the side-effects in animals of high dose levels of anticancer agents.

THE COMPOUND AND SALTS

The compound of this invention is 2,4-disulfonyl α-phenyl tertiary butyl nitrone. It is also referred to informally herein as "2,4-disulfon PBN" or "PBN 2,4-disulfonate." It exists in an acid form

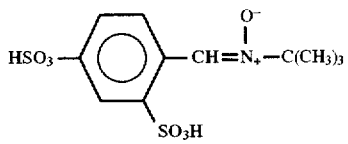

as a solid and in solution in low pH conditions. It also exists at higher pHs in an ionized salt form which can be shown as

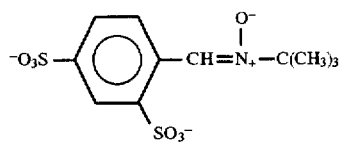

or as

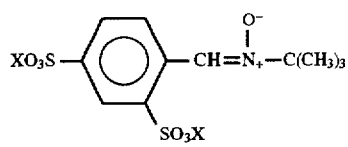

where X is a pharmaceutically acceptable cation. Most commonly, this cation is a monovalent material such as sodium, potassium or ammonium, but it can also be a multivalent cation alone or in combination with a pharmaceutically acceptable monovalent anion, for example calcium with a chloride, bromide, iodide, hydroxyl, nitrate, sulfonate, acetate, tartrate, oxalate, succinate, palmoate or the like anion; magnesium with such anions; zinc with such anions or the like. When these combinations of a polyvalent cation and a monovalent anion are illustrated in structural formulae, herein, the monovalent anion is identified as "Y".

Among these materials, the free acid and the simple sodium, potassium or ammonium salts are most preferred with the calcium and magnesium salts also being preferred but somewhat less so.

COMPOUND PREPARATION

As detailed in FIG. 1 and demonstrated in Example 1, the compound of this invention can be prepared by a two step reaction sequence. In the first step, commercially available tertiary butyl nitrate (2-methyl-2-nitropropane) is converted to the corresponding n-hydroxyl amine using a suitable catalyst such as an activated zinc/acetic acid catalyst or an aluminum/mercury amalgam catalyst. This reaction can be carried out in 0.5 to 12 hours and especially about 2 to 6 hours or so at a temperature of about 15° to 100° C. in a liquid reaction medium such as alcohol/water mixture in the case of the zinc catalyst or an ether/water mixture in the case of the aluminum amalgam catalyst.

In the second step, the freshly formed hydroxylamine is reacted with 4-formyl-1,3-benzenedisulfonic acid, typically with a slight excess of the amine being used. This reaction can be carried out at similar temperature conditions. This reaction is generally complete in 10 to 24 hours.

The product so formed is the free acid and is characterized by a molecular weight of 89 g/mole. It is a white powdery material which decomposes upon heating. It is characterized by a solubility in water of greater than 1 gram/ml and a $^1$H NMR spectrum in $D_2O$ of 8.048 ppm (dd, 8.4, 1.7 Hz); 8.836 ppm (d, 8.4 Hz); 8.839 ppm (d, 1.7 Hz); 8.774 ppm (s).

The various salts can be easily formed by admixing the free acid in aqueous medium with two equivalents of the appropriate base, for example, KOH for the potassium salt, and the like.

PHARMACEUTICAL COMPOSITIONS

The compound (including its salts) can be formulated into pharmaceutical compositions suitable for oral or parenteral, e.g. intravenous or intramuscular injection administration.

The compositions for oral administration can take the form of liquid solutions or suspensions, powders, tablets, capsules or the like. In such compositions, the PBN 2,4-disulfonate or its salt is usually a minor component (0.1 to say 50% by weight) with the remainder being various vehicles or carriers and processing aids helpful for forming the desired dosing form. A liquid form may include a suitable aqueous or nonaqueous vehicle with buffers, suspending dispensing agents, colorants, flavors and the like.

A solid form may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, sugar, methyl salicylate, or orange flavoring.

In the case of injectable compositions, they are commonly based upon injectable sterile saline or phosphate-buffered saline or other injectable carriers known in the art. Again the active nitrone is typically a minor component, often being from about 0.05 to 10% by weight with the remainder being the injectable carrier and the like.

Conditions Treated and Treatment Regimens

The conditions treated with the 2,4,disolfo PBN generally fall into three groups. The first includes conditions involving acute intense oxidative damage to a region of the central nervous system. Examples of these conditions include stroke, conditions associated with stroke, concussion and subarachnoid hemorrhage. In this setting, the compound is administered in a manner designed to get the drug into the patient's bloodstream as quickly and directly as possible. This usually means intravenous administration.

Intravenous dose levels for treating these conditions range from about 0.1 mg/kg/hour to at least 10 mg/kg/hour, all for from about 1 to about 120 hours and especially 24 to 96 hours. A preloading bolus of from about 10 to about 500 mg may also be administered to achieve adequate steady state levels.

While intravenous administration is preferred, other forms of parenteral administration, such as intramuscular injection can be used, as well. In this case, similar dose levels are employed. An unexpected and key advantage of 2,4,disulfo PBN is that it can be administered at vastly higher levels than are possible with PBN itself. As will be shown in the Examples, doses of up to 1000 mg/kg/hour and higher or intravenous bolus doses of from 10 to 2500 mg/kg have been demonstrated to be possible with 2,4,disulfo PBN or its salts while with PBN itself death or acute toxicity results from such doses. With 2,4,disulfo PBN there is an unexpected positive continuance of the dose/response curve in these high dose levels with the clear message that intense heavy dosing immediately post stroke or other trauma may in many cases provide a major positive impact upon recovery.

The second group of conditions which respond favorably to 2,4,disulfo PBN treatment are conditions characterized by protracted low grade oxidative stress upon the central nervous system and gradual progressive central nervous system function loss. These conditions include Alzheimer's disease, Parkinson's disease, amyotrophic lateral sclerosis (ALS), multi-infarct dementia, retinopathy and the like. Each of these conditions is characterized by a progressive loss of function. 2,4-disulfonyl-PBN or its salts, when administered orally or parenterally, e.g. intravenously, can slow and possibly reverse the loss of function. If parenteral, e.g. intravenous administration is desired, similar levels to those used with acute conditions but at the lower end of the ranges are generally used.

In these cases, the regimen for treatment may stretch over many months or years so oral dosing is preferred for patient convenience and tolerance. With oral dosing, one to three oral doses per day, each from about 0.02 to about 50 mg/kg are called for with preferred doses being from about 0.04 to about 5.0 mg/kg.

Of course, one can administer 2,4-disulfonyl PBN as the sole active agent or one can administer it in combination with other agents. This leads to a third application for this compound.

A third set of conditions which respond to treatment with 2,4,disulfo PBN are the side-effects which arise in patients from oxidative damage produced by cancer (neoplastic disease) therapy. The therapy which produces the oxidative damage (and thus the side effects) includes radiation (e.g. gamma radiation) therapy and therapy with oxidative-damage causing chemotherapeutic agents. Examples of these agents include antibiotics such as daunorubicin, doxorubicin and bleomycin; procarbazine; nitrogen mustards such as ifosfamide, melphalan and chlorambucil; alkylating agents; antimetabolites; hormones and antagonists.

Administration of 2,4,disulfo PBN can have the effect of reducing patient discomfort during these therapies. In addition, administration of the compound of this invention can increasing patients' ability to tolerate these therapies. Often the side effects of therapies force the discontinuance of these therapies or prevent the administration of optimal high doses or rapid frequencies of these therapies. In some cases these side effects are devastatingly destructive and lead to heart failure and other major function loss. In tests in animals it has been observed that the compound of the invention can improve patient tolerance of these antineoplastic disease treatments.

In this therapy, the compound of the invention may be administered before, during and after the radiation or chemotherapy is administered. Administration may be parenteral or oral or by any other method which will permit the 2,4-disulfonate PBN to enter the patient's bloodstream.

A positive dose-response relationship has been observed. As such, and bearing in mind the severity of the side effects and the advantages of providing maximum possible protection or amelioration, it may be desired in some settings to administer large amounts of 2,4,disulfo PBN such as those described above for the acute intense oxidative CNS damage conditions. In other settings lower doses, such as those set forth for the progressive neuronal disease therapy, may be used.

The following are examples of representative administration regimens: In monotherapy (adriamycin alone) two representative dose combinations are 10–600 mg Compound I per square meter area plus 60 mg adriamycin per square meter of surface area with adriamycin dosing occurring every seven or twenty-one days. Compound I may be administered before the adriamycin, for example, up to 60 minutes before, at the same time or after, such as hours after and on subsequent days. The pediatric dose is typically lower for both drugs. Higher doses may be used for treatment of multidose resistant tumors.

EXAMPLES

Example 1

Synthesis of 2,4-disulfophenyl-N-t-butylnitrone (Compound "I" in subsequent Examples). This preferred synthesis is based on the work by R. H. Hinton and E. G. Janzen (*J. Org. Chem.* 57:2646–2651, 1992). As shown in FIG. 1 it involves the condensation of an aldehyde with a hydroxylamine. The hydroxylamine is unstable and is prepared fresh on the day of use using an activated zinc catalyst. The synthesis is as follows:

Prerequisite Chemicals 1. 95% Ethanol
2. 2-Methyl-2-nitropropane
3. Zinc dust
4. Glacial acetic acid
5. Diethyl ether
6. Saturated sodium chloride
7. Magnesium Sulfate, Anhydrous solid
8. 4-Formyl-1,3-benzenesulfonic acid (MW 310.21 g/mole), disodium salt, hydrate
9. Methanol
10. Dichloromethane

Procedure

A. Preparation of N-t-Butylhydroxylamine

1. A 500 ml three neck round bottom flask is equipped with a magnetic stir bar, thermometer adapter, thermometer, and addition funnel.
2. 95% ethanol (350 ml) was added to the flask and cooled to 10° C. in an ice bath.
3. 2-Methyl-2-nitropropane (6.18 g, 0.060 mole), and zinc dust (5.89 g, 0.090 mole) were added in single portions.
4. Glacial acetic acid (10.8 g, 0.180 mole) was placed in the addition funnel and added dropwise at such a rate with vigorous stirring to maintain the temperature below 15° C.
5. The ice bath was removed and mixture was stirred for 3 hrs at room temperature.
6. The solvent was stripped from the mixture, leaving t-butylhydroxylamine, zinc acetate, and water.
7. Dichloromethane (50 ml) was added and the mixture filtered through a Buchner funnel.
8. The zinc acetate cake left on the filter paper was washed with 2×25 ml dichloromethane.

9. Water was separated from the filtrate in a separatory funnel and the organic layer dried over magnesium sulfate.

10. The magnesium sulfate was removed by filtering through fluted filter paper, then dichloromethane stripped off by rotary evaporation.

11. The product (100% yield=5.34 g), a viscous liquid, was dissolved in methanol (50 ml) for use in part B.

B. Preparation of 2,4-disulfonylphenyl-N-t-butylnitrone

1. A 3-neck 250 ml round bottom flask was set up with a stir bar, a gas dispersion tube, an addition funnel, and a Friedrichs condenser cooled with recirculating ice water.

2. To the flask were added 200 ml of methanol, 4-formyl-1,3-benzenedisulfonic acid (9.31 g, 30 mmoles) and N-t-butylhydroxylamine (25 ml of the methanol solution from part A, 30 mmoles theoretical).

3. The reaction was heated to reflux with a heating mantle while bubbling the reaction with nitrogen with stirring.

4. The mixture was refluxed for 2 hours.

5. The remainder of hydroxylamine from part A was added.

6. Refluxing was continued with nitrogen bubbling for at least 18 hours, but not more than 24 hours.

7. The hot reaction mixture was filtered on a Buchner funnel, and the solid washed with hot methanol.

8. The methanol was stripped off by rotary evaporation to a yellow, viscous oil.

9. Hot 1:1 ethanol:acetone (200 ml) was added and the mixture heated to dissolve the oil.

10. The solution was cooled to crystallize the product.

11. The product was collected on a Buchner funnel and dried under vacuum overnight.

12. The reaction typically gives 75% yield of Compound I, a white powder.

Example 2

Alternate Synthesis of 2,4-disulfonylphenyl-N-t-butylnitrone (Compound I). This is an earlier-developed method which used to prepare samples of the compound used in several of the experiments reported in the Examples of this specification. The product of this Example is identical in all ways to the product of Example 1. This synthesis method is as follows:

Prerequisite Chemicals

1. Aluminum Foil, cut into 5 cm wide strips and rolled in a ca. 1 cm diameter cylinder
2. Mercury (II) Chloride (9.68 g in 476 ml water)
3. Ethanol
4. Ether (6 l)
5. Pure Water
6. 2-Methyl-2-nitropropane
7. Sodium Hydroxide, 2M (80 g in 1l water)
8. Magnesium Sulfate, Anhydrous solid
9. 4-Formyl-1,3-benzenesulfonic acid (MW 310.21 g/mole)

Procedure

A. Preparation of N-t-Butylhydroxylamine

1. Aluminum foil cylinders were dipped into $HgCl_2$ solution for 15-30 seconds, then dipped in ethanol, then dipped in ether and then placed into a 5 l flask containing 500 ml of diethyl ether and 21.4 ml of water.

2. The flask was fitted with a 250 ml pressure-equalizing dropping funnel, a mechanical stirrer, a nitrogen inlet, and a Friedrichs condenser cooled with recirculated ice water.

3. The mixture was stirred for 10 minutes.

4. 2-Methyl-2-nitropropane (71.68 g, 75.5 ml) was added using the dropping funnel at such a rate as to maintain a vigorous reflux.

NOTE: Addition must be completed in less than 20 minutes or the yield drops significantly.

5. As the addition proceeded, ether was added in 500 ml portions. This was done to maintain as high a concentration of product as possible without the formation of a gel. Up to 2 l of ether can be added with no deleterious effects on the yield.

6. Once addition of 2-methyl-2-nitropropane was complete, the reaction was stirred for an additional 30 minutes.

7. The resulting gray suspension was suction filtered in 3 batches to remove aluminum salts.

8. Each filter cake was washed with 1 l of ether.

9. The combined either layers were washed with 300 ml of 2M NaOH, then dried ($MgSO_4$), and concentrated in vacuo to leave a soft white solid.

10. The solid melts just above room temperature, but could be dried further in a vacuum oven (no more than a few minutes), leaving 38 to 45 g of solid.

11. The solid can be used as is or was purified by recrystallization from pentane.

12. Molecular weight—89 g/mole.

B. Preparation of 2,4-disulfonylphenyl-N-t-butylnitrone

1. A 250 ml flask was equipped with a stir bar and a Friedrichs condenser cooled with recirculated ice water.

2. The flask was charged with 71.8 ml of methanol, 14.5 g of 4-formyl-1,3-benzenedisulfonic acid (46.7 mmoles, 1 eq.), and 5.0 g of N-t-butylhydroxylamine (56.2 mmoles, 1.2 eq.).

3. The mixture was refluxed overnight.

4. The reaction product was transferred to round-bottom flask and rotovaped to dry.

5. The solid residue was mashed with ether, the ether was decanted off (yellow).

6. Step 5 was repeated.

7. Product ("Compound I") was crystallized from methanol following a hot methanol filtration to remove insoluble precipitates and recrystallized twice from methanol.

Example 3

A series of experiments were carried out to compare in vivo the efficacy of 2,4 disulfo PBN ("Compound I"), PBN, and two monosulfonate PBN compounds as agents for protecting against neuron loss following brain ischemia and reperfusion injury. The test procedure is that reported by W. Cao, J. M. Carney, A. Duchon, R. A. Floyd and M. Chevion as "Oxygen free radical involvement in ischemia and reperfusion injury to brain, Neuroscience Letters, 88 (1988), 233. In the experiments a test compound was administered to groups of six gerbils i.p. as a single dose 30 min before 5 min bilateral carotid occlusion. The density of neuronal nuclei in a 100 micron was measured. Two controls were present—controls which received no test compound and controls which received no test compound and no brain ischemia. As illustrated in Table 1. the compound of the invention showed unexpected advantages as compared to the prior art compounds. First, it is seen that at low dose levels, such as 3.2 mg/kg, compound I is 2–3 times as potent at preventing neuronal loss. At high dose levels it is seen that Compound I is able to achieve complete protection against neuronal loss as the test brains showed neuronal densities identical to the non-ischemic controls. The prior art compounds are either toxic at these dose levels or showed significantly lower degrees of protection. These results show a clear increase in potency for neural protection for compound I compared to PBN and two closely related analogs and an unexpected decrease in toxicity compared to PBN.

TABLE 1

| | Neuronal nuclei/100 micron field | | | |
|---|---|---|---|---|
| | PBN | 2-sulfo | 3-sulfo | Cmpd. I |
| Non-ischemic control | 4.21 | 4.21 | 4.21 | 4.21 |
| | (.43) | (.43) | (.43) | (.43) |
| Ischemic control | 0.58 | 0.58 | 0.58 | 0.58 |
| | (.28) | (.28) | (.28) | (.28) |
| 3.2 mg/kg | 0.43 | 0.73 | 0.35 | 1.43 |
| | (.18) | (.34) | (.21) | (.31) |
| 10 mg/kg | 1.13 | 0.68 | 0.81 | 2.57 |
| | (.39) | (.31) | (.40) | (.25) |
| 32 mg/kg | 1.83 | 0.73 | 1.63 | 3.53 |
| | (.21) | (.31) | (.35) | (.41) |
| 50 mg/kg | 3.11 | 1.01 | 1.63 | 4.11 |
| | (.29) | (.61) | (.35) | (.43) |
| 100 mg/kg | 3.68 | 0.93 | 1.93 | 4.18 |
| | (.71) | (.53) | (.39) | (.49) |
| 320 mg/kg | 3.78 | 1.11 | 1.78 | 4.23 |
| | (.43) | (.41) | (.40) | (.39) |
| 1000 mg/kg | Toxic | 0.98 | 1.58 | 4.11 |
| | | (.43) | (.38) | (.41) |
| 3200 mg/kg | Toxic | — | — | 4.18 |

Example 4

A series of experiments were conducted in which compound I was compared to PBN and two sulfonate analogs in post-ischemia treatment. The general method described in example 1 was used but the test compounds were administered i.p. as a single dose 30 min after reperfusion following 5 min ischemia. The results are summarized in Table 2. Table 2 shows that the compound of the invention is again more potent at low doses and more potent and less toxic at high doses. Also again, toxicity interferes with the ability of the prior art compounds to go to high doses at which levels the compound of the invention provides dramatically effective therapy.

TABLE 2

| | Neuronal nuclei/100 micron field | | | |
|---|---|---|---|---|
| | PBN | 2-sulfo | 3-sulfo | Cmpd. I |
| Non-ischemic control | 4.18 | 4.18 | 4.18 | 4.18 |
| | (.59) | (.59) | (.59) | (.59) |
| Ischemic control | 0.85 | 0.85 | 0.85 | 0.85 |
| | (.19) | (.19) | (.19) | (.19) |
| 32 mg/kg | 1.09 | ND | ND | 1.83 |
| | (.31) | | | (.41) |
| 50 mg/kg | 1.85 | 0.68 | 0.73 | 2.73 |
| | (.49) | (.31) | (.34) | (.39) |
| 100 mg/kg | 2.11 | 0.78 | 1.09 | 3.41 |
| | (.51) | (.23) | (.48) | (.37) |

TABLE 2-continued

| | Neuronal nuclei/100 micron field | | | |
|---|---|---|---|---|
| | PBN | 2-sulfo | 3-sulfo | Cmpd. I |
| 320 mg/kg | 2.25 | 0.81 | 0.93 | 3.55 |
| | (.43) | (.31) | | (.48) |
| 1000 mg/kg | Toxic | ND | ND | 3.68 |
| | | | | (.39) |

Example 5

Compound I is compared with PBN to determine the relative effectiveness for protection of neuronal loss when administered i.v. 60 min after reperfusion onset following 5 min ischemia in gerbils using the general test method described in Example 1.. The results are summarized in Table 3. and illustrate that compound I is of significantly greater therapeutic benefit in a clinical treatment setting following injury to the brain.

TABLE 3

| N = 6 per group | mg/kg single dose | | | |
|---|---|---|---|---|
| | 0.0 | 0.5 | 1.0 | 10 |
| Saline, no ischemia | 4.11 | — | — | — |
| | (.28) | | | |
| saline, ischemia | 0.93 | — | — | — |
| | (.17) | | | |
| PBN | — | 0.83 | 1.07 | 1.23 |
| | | (.23) | (.29) | (.31) |
| Compound I | — | 1.25 | 1.75 | 2.43 |
| | | (.19) | (.28) | (.31) |

Neither PBN nor Compound I. had an effect on neuronal density in control gerbils without brain injury.

Example 6

Brain injury can manifest itself as behavioral changes. In this experiment, young adult (3–4 months of age) gerbils were tested to determine their ability to perform an 8-arm maze test 24 hours following an ischemic event as described in Example 1. As compared to nonischemic animals, when untreated they committed many more errors. PBN and compound I were administered to some of the test animals. As detailed in Table 4, gerbils treated with high doses of compound I had error levels indistinguishable from those of nonischemic animals. PBN was less effective. This shows that compound I can protect against the loss of temporal/spatial short term memory following ischemia (24 hours post) errors in 8-arm radial maze test of young gerbils following 5 min ischemia.

TABLE 4

| N = 6 per group | mg/kg/hr for 24 hours | | | | |
|---|---|---|---|---|---|
| | 0.0 | 1.0 | 32 | 50 | 100 |
| Control | 4.1 | — | — | — | — |
| | (.38) | | | | |
| Postischemic | 37.6 | — | — | — | — |
| | (4.85) | | | | |
| PBN | — | 29.8 | 18.19 | 6.23 | 5.83 |
| | | (7.27) | (5.83) | (.71) | (.49) |
| Compound I | — | 14.63 | 7.19 | 4.28 | 4.11 |
| | | (3.81) | (.81) | (.29) | (.19) |

Example 7

The ability of the compound of the invention to reduce infarct volume following an ischemic event was determined. As detailed in Table 5, it was observed that while PBN and compound I were both effective at low doses, at high doses I gave the best protection and PBN was toxic. Table 5 shows the infarct volume observed when test compound was administered i.v. 60 min after middle cerebral occlusion and continued for 24 hours in C57BL/6J mice.

TABLE 5

|  | Infarct Volume in mm³ | | | |
| --- | --- | --- | --- | --- |
| Posttreatment (mg/kg/hr) | 0.0 | 1.0 | 10 | 100 |
| Control, no ischemia | 0 | — | — | — |
| Saline, ischemia | 23 (2) | — | — | — |
| PBN | — | 17.7 (2.8) | 13.8 (2.3) | Toxic |
| Compound I | — | 16.8 (1.7) | 12.7 (3.93) | 8.3 (.71) |

Example 8

In this study, compound I and PBN are compared for their ability to impart lethality protection (% survived) in aged gerbils (18–24 months of age, n=12/group) from 10 min ischemia when given 30 min before ischemia. As shown in Table 6, compound I is superior at all dose levels and achieved complete protection at high levels while PBN is only partially effective.

TABLE 6

| Pretreatment (mg/kg) | 0.0 | 10 | 32 | 100 | 320 |
| --- | --- | --- | --- | --- | --- |
| Saline | 11 | — | — | — | — |
| PBN | — | 42 | 50 | 75 | 92 |
| Compound I | — | 50 | 75 | 100 | 100 |

Example 9

An important advantage of the compound of this invention as compared to the art-taught compound, PBN, is its markedly diminished toxicity. As detailed in Table 7, acute lethality in C57BL/6L mice was determined based upon varying sizes of single i.p. doses of nitrone. PBN showed significant toxicity at 560 mg/kg dose levels. Compound I showed no toxicity at doses nearly twenty times as great.

TABLE 7

|  | mg/kg | | | | |
| --- | --- | --- | --- | --- | --- |
| % Survival n = 20 mice | 320 | 560 | 1000 | 3000 | 10000 |
| PBN | 100 | 25 | 0 | 0 | 0 |
| Compound I | 100 | 100 | 100 | 100 | 100 |

Example 10

Another undesirable systemic effect which has been observed in vivo with nitrone radical traps is a depression in body temperature. This toxicity can have serious health consequences and also can complicate diagnosis of other conditions. As detailed in FIGS. 2 and 4, the compound of this invention was administered to mice and gerbils at levels as high as 1000 mg/kg with no measurable temperature decrease. In contrast, the compound of the art, PBN, gave up to an 8° C. decrease in body temperature at a does of only 500 mg/kg.

Example 11

The compound of the invention was tested to determine its effectiveness in the treatment of conditions characterized by protracted low grade oxidative stress upon the central nervous system and gradual progressive central nervous system function loss by testing its effectiveness in a model for Alzheimer's disease ("AD"). This model has the following basis: Recent studies have demonstrated that there is an age-associated increase in protein oxidation and loss of enzyme activities in the brain of aged individuals. Tissue cultures of fibroblasts from aged individuals and red blood cells of different ages both show an exponential increase in protein carbonyl content (a measure of protein oxidation) and a decrease in marker enzyme activities. Brain protein oxidation progressively increases over the life span of the individual.

The role of abnormal amyloid precursor peptide processing and metabolism in AD has also been explored in a number of different models. In vitro studies using embryonic hippocampal neuronal and neuronal/glial cultures have demonstrated that βAP 1–40 produces cytotoxicity over an extended period of co-incubation. When this peptide is infused into rat brains, lesions are produced. Some of the proposed breakdown fragments of βAP are also neurotoxic [e.g. PAP (25–35)]. The neurotoxicity appears to be both mediated via glutamate receptors, and also by non-glutamate receptors mechanisms. Confocal microscopy studies of neuronal cultures have demonstrated that exposure to βAP (1–40) results in oxidative stress [Dichlorofluorescein and increased intracellular free calcium Fura-2].

It has been demonstrated that βAP fragments can directly inactivate glutamine synthetase (GS) and creatine kinase (CK) in tissue extracts and in cultured hippocampal neurons and glia (See A and B in FIG. 4). A and B of FIG. 4 present the dose-related inactivation of glutamine synthetase and creatine kinase by AP (25–35). Cytosolic fractions from gerbil neocortex were prepared and enzyme activities determined. Samples were incubated in the presence of different concentrations of the peptide for 10 min prior to assay. Solid symbols represent the effects of the naturally occurring 25–35 fragment. Open circles indicate that the reverse sequence (32–25) had no effect on enzyme activity. Open triangles indicate that the scrambled amino acid sequence also had no effect on enzyme activities, compared to the effect of 25–35. Each point is the mean (+/− s.e.) of 5 observations. βAP derived and other cellular sources of free radicals are an important determinant of the initiation and progression of AD.

As demonstrated in C and D in FIG. 4, compound I and PBN each show the ability to protect GS and CK against the effects of βAP fragments. C and D of FIG. 4 present the protective effects of co-incubation of the cytosolic fractions with BAP 25–35 (0.4 mg/ml) in combination with different concentrations of PBN (open circles) or compound I (closed circles). Each point is the mean (+/− s.e.) of 3 observations. As can be seen in C and D, compound I gives complete protection and in fact might even be able to reverse the effects of oxidation. In contrast, PBN's effectiveness is quite limited as it is asymptotically leveling out at a substantially incomplete level of protection.

Example 12

Experiments were carried out to further demonstrate the effectiveness of the compound of the invention in preventing central nervous system damage caused by stroke.

Rat Focal Ischemia Results

A pair of studies were done to determine the efficacy of Compound I in a rat focal ischemia model. In this model, Sprague Dawley rats (200–300 g) underwent a permanent middle cerebral artery occlusion (MCAO) to induce a focal stroke. Compound I was administered after the permanent occlusion as first an intraperitoneal (i.p.) bolus dose and then by intravenous (i.v.) continuous infusion during the remaining time up to 24 hours post stroke. The doses of Compound I used were either 100 mg/kg, i.p., followed by 4.2 mg/kg/hr, i.v., or 10 mg/kg, i.p., followed by 0.42 mg/kg/hr, i.v.

The rats were sacrificed 3 days post stroke, the tissue was processed histologically using triphenyltetrazolium staining techniques, and the infarct volume, the area of total cell necrosis, was quantitated using image analysis. The results of these experiments are shown graphically in FIG. 5 and demonstrate that Compound I provided significant protection, approximately 70%, in both studies.

Comparison with Results in the Literature.

Similar data have been reported recently for the compound NOT of this invention, PBN, by Cao and Phillis (Brain Research 664: 267–272, 1994). In their studies, rats underwent a permanent middle cerebral artery occlusion (MCAO) and a common carotid artery occlusion. The PBN was administered i.p. at 100 mg/kg at various times post stroke. The rats were sacrificed 2 days post stroke and the infarct volume was quantitated using triphenyltetrazolium stain.

When PBN was administered at 0.5, 5, 17, 29 and 41 hours post stroke, or at 5, 17, 29, and 41 hours post stroke, the infarct volume was reduced in each case by approximately 50%. The cumulative dose of PBN administered to achieve 50% protection is at a minimum 4 times the amount of Compound I required for 70% protection. Thus, Compound I is far superior to PBN in offering protection in the rat MCAO focal ischemia model.

Example 13

In this Example the compound of this invention (Compound I) was evaluated to determine its ability to ameliorate oxidation-caused side effects of anticancer therapy.

Adriamycin Studies

Adriamycin is a widely used anticancer agent. It is known to be very effective but it is also known to have serious side effects arising from its tendency to cause oxidative damage. These side effects include causing serious levels of cardiac damage at high dose levels. These side effects have often limited the use of this agent or limited the dose levels that can be employed to levels which are below those desired for maximum antineoplastic disease effectiveness.

Experiments were carried out to demonstrate that the compound of the invention is effective at reducing the side effects of anticancer agents such as adriamycin and permitting higher dose levels of adriamycin to be tolerated by animals.

C57BL/6J and DBA/2J male mice (35–40 g) were tested for the acute lethal effects of adriamycin and the prevention of acute lethality by pretreatment doses of Compound I. Mice were injected with either saline or Compound I 30 minutes prior to administration of adriamycin. All injections were intraperitoneal. The acute lethality of adriamycin ranged from 10 to 30 mg/kg. The $LD_{50}$ for adriamycin in these tests was found to be 25 mg/kg in both mouse strains. Compound I doses up to 300 mg/kg, without adriamycin treatment, had no effect on survival in the two mouse strains.

Pretreatment with 30 and 100 mg/kg of Compound I produced dose related shifts in the adriamycin lethality dose effect curve. FIG. 6 shows the results obtained using the DBA/2J mouse. A dose of 100 mg/kg of Compound I produced a 5-fold shift to the right (in the direction of reduced lethality). Thus, the combination of Compound I with adriamycin resulted in a marked increase in the maximally tolerated dose. These higher doses are in the range that would effectively kill multi-drug resistant tumors.

Comparative Tests

PBN pretreatment resulted in a slight shift to the right in the adriamycin does-effect curve. While the Compound I dose could be increased to 300 mg/kg in combination with adriamycin, there was an upper limit for this combination with PBN. A dose of PBN of 100 mg/kg produced slight sedation and 300 mg/kg yielded marked sedation and some combined toxicity (10–20% lethality). Compound I/adriamycin did not produce any combined toxicity at doses of Compound I of up to 300 mg/kg.

Example 14

Safety Testing.

Compound I and PBN were tested for their acute toxicity in male Sprague Dawley (200–300 g) rats. The compounds were administered at 1000 mg/kg, i.p., to groups of 6 rats. After 3 days lethality was assessed. Compound I caused no lethality, while PBN was lethal to 5 of the 6 rats used in this test. These data confirm the gerbil data in that Compound I has higher safety than PBN.

What is claimed is:

1. A method for treating a patient who has suffered a concussion comprising administering to said patient an effective concussion treating amount of a pharmaceutical composition comprising the compound 2,4-disulfo alpha-phenyl tertiary butyl nitrone in a pharmaceutically acceptable carrier.

2. The method of claim 1 wherein the composition is administered parenterally.

3. The method of claim 2 wherein the composition is administered intraveneously.

4. The method of claim 3 wherein the composition is administered in an amount of at least 0.2 mg/kg/hour.

5. The method of claim 1 wherein the composition is administered orally.

6. A method for treating a patient who has suffered a concussion comprising administering to said patient an effective concussion treating amount of a pharmaceutical composition comprising a compound of the formula:

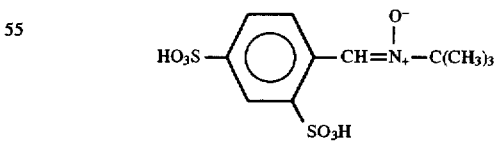

in a pharmaceutically acceptable carrier.

7. The method of claim 6 wherein the composition is administered parenterally.

8. The method of claim 7 wherein the composition is administered intraveneously.

9. The method of claim 8 wherein the composition is administered in an amount of at least 0.2 mg/kg/hour.

10. The method of claim 6 wherein the composition is administered orally.

11. A method for treating a patient who has suffered a concussion comprising administering to said patient an effective concussion treating amount of a pharmaceutical composition comprising a pharmaceutically acceptable salt of:

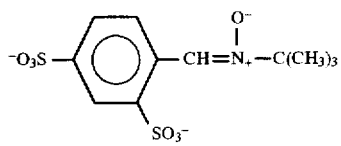

in a pharmaceutically acceptable carrier.

12. The method of claim 11 wherein the composition is administered parenterally.

13. The method of claim 12 wherein the composition is administered intraveneously.

14. The method of claim 13 wherein the composition is administered in an amount of at least 0.2 mg/kg/hour.

15. The method of claim 11 wherein the composition is administered orally.

16. A method for treating a patient who has suffered a concussion comprising administering to said patient an effective concussion treating amount of a pharmaceutical composition comprising a compound of the formula:

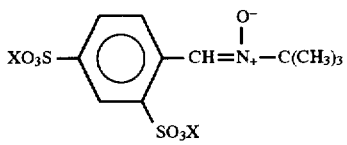

wherein X is selected from the group consisting of Na, K, $NH_4$, Ca, Mg, Zn, ZnY, CaY and MgY, wherein Y is a pharmaceutically acceptable monovalent anion, in a pharmaceutically acceptable carrier.

17. The method of claim 16 wherein the composition is administered parenterally.

18. The method of claim 17 wherein the composition is administered intraveneously.

19. The method of claim 18 wherein the composition is administered in an amount of at least 0.2 mg/kg/hour.

20. The method of claim 16 wherein the composition is administered orally.

21. A method for treating a patient who is suffering from a subarachnoid hemorrhage comprising administering to said patient an effective subarachnoid hemorrhage treating amount of a pharmaceutical composition comprising the compound 2,4-disulfo alpha-phenyl tertiary butyl nitrone in a pharmaceutically acceptable carrier.

22. The method of claim 21 wherein the composition is administered parenterally.

23. The method of claim 22 wherein the composition is administered intraveneously.

24. The method of claim 23 wherein the composition is administered in an amount of at least 0.2 mg/kg/hour.

25. The method of claim 21 wherein the composition is administered orally.

26. A method for treating a patient who is suffering from a subarachnoid hemorrhage comprising administering to said patient an effective subarachnoid hemorrhage treating amount of a pharmaceutical composition comprising a compound of the formula:

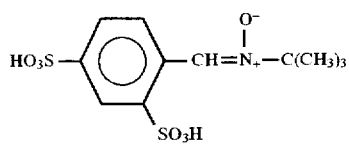

in a pharmaceutically acceptable carrier.

27. The method of claim 26 wherein the composition is administered parenterally.

28. The method of claim 27 wherein the composition is administered intraveneously.

29. The method of claim 28 wherein the composition is administered in an amount of at least 0.2 mg/kg/hour.

30. The method of claim 26 wherein the composition is administered orally.

31. A method for treating a patient who is suffering from a subarachnoid hemorrhage comprising administering to said patient an effective subarachnoid hemorrhage treating amount of a pharmaceutical composition comprising a pharmaceutically acceptable salt of:

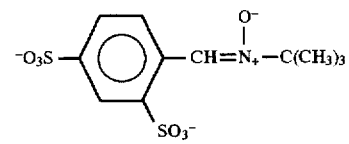

in a pharmaceutically acceptable carrier.

32. The method of claim 31 wherein the composition is administered parenterally.

33. The method of claim 32 wherein the composition is administered intraveneously.

34. The method of claim 33 wherein the composition is administered in an amount of at least 0.2 mg/kg/hour.

35. The method of claim 31 wherein the composition is administered orally.

36. A method for treating a patient who is suffering from a subarachnoid hemorrhage comprising administering to said patient an effective subarachnoid hemorrhage treating amount of a pharmaceutical composition comprising a compound of the formula:

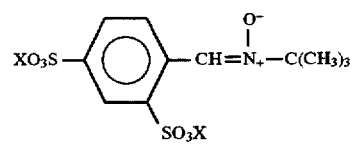

wherein X is selected from the group consisting of Na, K, $NH_4$, Ca, Mg, Zn, ZnY, CaY and MgY, wherein Y is a pharmaceutically acceptable monovalent anion, in a pharmaceutically acceptable carrier.

37. The method of claim 36 wherein the composition is administered parenterally.

38. The method of claim 37 wherein the composition is administered intraveneously.

39. The method of claim 38 wherein the composition is administered in an amount of at least 0.2 mg/kg/hour.

40. The method of claim 36 wherein the composition is administered orally.

* * * * *